United States Patent
Saguto

(10) Patent No.: US 7,159,470 B2
(45) Date of Patent: Jan. 9, 2007

(54) SYSTEMS AND METHODS OF MEASURING RESIDUAL STRESS IN METALLIC MATERIALS

(75) Inventor: Gregory P. Saguto, St. Charles, MO (US)

(73) Assignee: The Boeing Company, Chicago, IL (US)

(*) Notice: Subject to any disclaimer, the term of this patent is extended or adjusted under 35 U.S.C. 154(b) by 75 days.

(21) Appl. No.: 11/134,170

(22) Filed: May 20, 2005

(65) Prior Publication Data

US 2006/0260412 A1    Nov. 23, 2006

(51) Int. Cl.
G01B 7/16    (2006.01)
G01B 1/00    (2006.01)

(52) U.S. Cl. ...................................................... 73/779
(58) Field of Classification Search ................... 73/779
See application file for complete search history.

(56) References Cited

U.S. PATENT DOCUMENTS

| | | | |
|---|---|---|---|
| 4,095,103 A * | 6/1978 | Cohen et al. ............... | 378/72 |
| 4,528,856 A | 7/1985 | Junker et al. | |
| 4,686,631 A * | 8/1987 | Ruud ......................... | 702/42 |
| 4,706,020 A | 11/1987 | Viertl et al. | |
| 4,856,326 A | 8/1989 | Tsukamoto | |
| 4,893,079 A | 1/1990 | Kustra et al. | |
| 5,055,784 A | 10/1991 | Jaeger et al. | |
| 5,184,071 A | 2/1993 | Tasca | |
| 5,610,515 A | 3/1997 | Soules | |
| 5,616,857 A | 4/1997 | Merck, Jr. et al. | |
| 5,666,051 A * | 9/1997 | Junker et al. .............. | 324/209 |
| 5,898,302 A | 4/1999 | Soules | |
| 6,142,010 A | 11/2000 | Merck, Jr. et al. | |
| 6,247,355 B1 | 6/2001 | Suresh et al. | |
| 6,247,356 B1 | 6/2001 | Merck, Jr. et al. | |
| 6,583,618 B1 | 6/2003 | McClelland | |
| 6,718,820 B1 | 4/2004 | Kwon et al. | |
| 6,727,690 B1 | 4/2004 | Soules | |
| 6,851,300 B1 * | 2/2005 | Kwon et al. ................ | 73/85 |

* cited by examiner

*Primary Examiner*—Michael T. Cygan
*Assistant Examiner*—Octavia Davis
(74) *Attorney, Agent, or Firm*—Lee & Hayes, PLLC

(57) ABSTRACT

Systems and methods of measuring residual stress are disclosed. In one embodiment, a method of measuring residual stress in a material under test includes directing radiation onto a stressed material and detecting the resulting diffraction peaks to measure known residual stress of a control specimen, inducing and sensing magnetoelastic interactions onto the control specimen, developing an empirical database of the diffraction and magnetoelastic interaction measurements of the control specimen, inducing and measuring magnetoelastic interactions on a material under test, and correlating the empirical database to the magnetoelastic interaction outputs from the material under test.

16 Claims, 4 Drawing Sheets

SYSTEMS AND METHODS OF MEASURING RESIDUAL STRESS IN METALLIC MATERIALS

GOVERNMENT LICENSE RIGHTS

This invention was made with Government support under U.S. Government contract N00019-02-C-3044 awarded by United States Navy. The Government has certain rights in this invention.

FIELD OF THE INVENTION

The present disclosure relates generally to systems and methods of measuring residual stress and, more specifically, to measuring residual stress in metallic materials.

BACKGROUND OF THE INVENTION

The different magnitudes of stress throughout an object are known as residual stress. The name comes primarily from the fact that residual stress is the stress remaining within an object as a result of service induced overloads, forming, shaping or other processing that changes the internal residual stress of an object. Objects are generally formed by exposure to a change in energy, heat, or an application of pressure. Whenever an object is exposed to such a change or local deformation occurs, residual stresses may change. This change in residual stress effects the atoms within the object by increasing or decreasing the spatial configuration between neighboring atoms.

Quantifying the residual stresses present in a component, which may either accelerate or arrest fatigue, fracture, distortion, wear, creep, or stress corrosion cracking, is frequently crucial to understanding a cause of failure in a component part. Current methods of measuring residual stress calculate the surface changes of a pre-existing surface. Because the measurements are indirect representations of displacement at the surface, the residual stress calculations are theoretically complex and tedious, and can only be performed on nonplated and noncoated parts. For example, in some methods, a material is subjected to radiation and a series of resulting diffraction peaks are measured to determine the distance between atoms and/or lattice planes. Strength related characteristics, such as stress, retained austenite, hardness, level of fatigue, etc can affect this measurement. Diffraction methods alone may be limited to measuring across a large number of positions on the material to obtain unrevealing information, particularly where the material being tested has been used in the field where corrosion and other environmental use conditions can cause highly localized variations in the strength characteristics being determined. When the only measurements taken include such localized aberrations, the determination of residual stress within a material can be effected.

Furthermore, it may also be desirable to quantify residual stress of a metallic material having layers applied to the pre-existing surface, including, for example, layers of protective coating, corrosive resistant plating, paint and primer.

SUMMARY

The present invention is directed to systems and methods of measuring residual stress. Embodiments of the present invention may provide accurate and meaningful measurements of residual stress in metallic materials, including in plated and coated metallic materials, which help may significantly reduce exposure to corrosion.

In one embodiment, a method of measuring residual stress in a material under test includes developing an empirical database using measurements from a plurality of specimens having known residual stress using at least one of diffraction values and magnetoelastic interaction values; directing radiation onto a stressed material and causing diffraction peaks; detecting the diffraction peaks; inducing magnetoelastic interactions within the stressed coated material; sensing the magnetoelastic interactions; and determining a residual stress within the material under test by comparing at least one of the diffraction peaks and the magnetoelastic interactions with the empirical database.

BRIEF DESCRIPTION OF THE DRAWINGS

Preferred and alternate embodiments of the present invention are described in detail below with reference to the following drawings.

DETAILED DESCRIPTION

The present invention relates to systems and methods of measuring residual stress in metallic materials. Many specific details of certain embodiments of the invention are set forth in the following description and in FIGS. 1–4 to provide a thorough understanding of such embodiments. One skilled in the art, however, will understand that the present invention may have additional embodiments, or that the present invention may be practiced without one or more of the details described in the following description.

Figure 1:
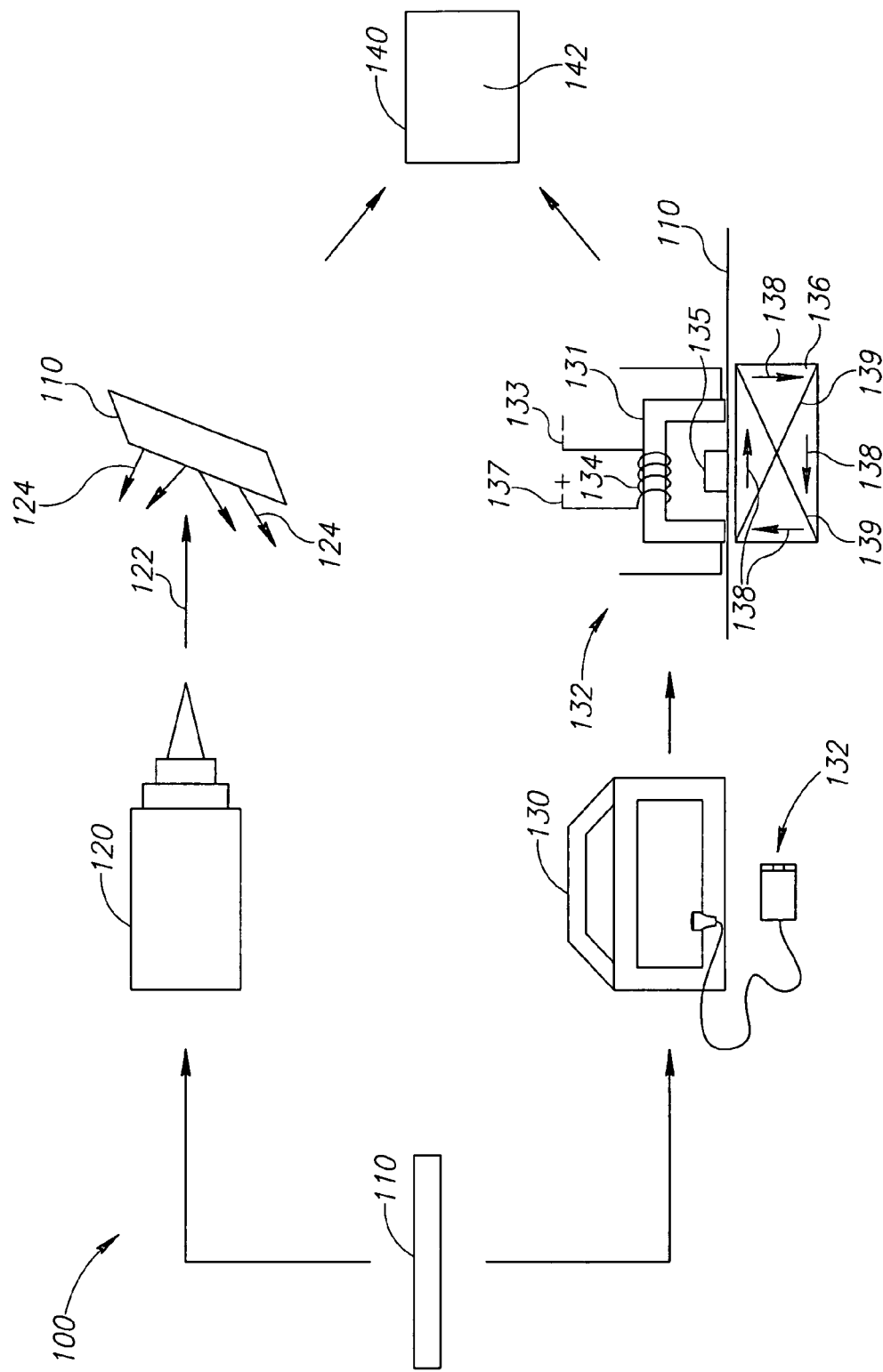
FIG. 1 is a schematic view of a system for measuring residual stress in a metallic material according to an embodiment of the present invention.

FIG. 1 is a schematic view of a system 100 for measuring residual stress in a stressed material 110 according to an embodiment of the present invention. In one aspect, the system 100 includes a radiation device 120, an electromagnetic assembly 130, and a data reduction system 140 for combining the measurements of the radiation device 120 and the electromagnetic assembly 130. The radiation device 120 directs radiation 122 onto the stressed material 110 and detects the resulting diffraction peaks 124. In one particular embodiment, the radiation device 120 may comprise an x-ray diffraction device. An x-ray diffraction device typically measures residual stress by directing an x-ray beam onto a work piece (i.e. a stressed material) and causing the beam to be diffracted, creating observable diffraction peaks. If the material is stress free, the peaks occur at a specific known angle depending on the wavelength of the x-ray and the material being analyzed. If the peaks shift, then the shifted angle may be used as a measurement of the amount of stress present in the material. The degree and location of the shift may provide data that allows calculation of how much the material has either pulled apart (tensile stress) or pushed together (compressive stress). Diffraction devices 120 may be used for determining the integrity of manufacturing components such as bearings, gears, springs and other suitable work pieces.

An electromagnetic assembly 130 includes a sensor head 132. In one particular embodiment, the sensor head 132 includes a magnetizable member 131. An electrically conductive wire 133 is formed in a coil 134 around at least a portion of the magnetizable member 131. An alternating current 137 passes through the wire 133, creating an alternating magnetic field within the magnetizable member 131, which in turn, induces a magnetic field (not shown) within the stressed material 110. In one particular embodiment, the alternating magnetic field created by the sensor head 132 has an alternating frequency of 3–15 KHz. A sensing unit 135 may be proximately positioned to the stressed material 110 to measure the induced Barkhausen Noise created within the stressed material 110 due to magnetoelastic interactions. Thus, the sensor head 132 may be used to sense surface and subsurface interactions of the stressed material 110. In one embodiment, the sensor may comprise a rollscan inspection device. Appropriate rollscan inspection devices may include, for example, the Stressscan® 500C, the Rollscan® 100, the Rollscan® 200, the Rollscan® 300 and the µScan 500 manufactured by American Stress Technologies, Inc. of Pittsburgh, Pa., as disclosed in detail in the U.S. Pat. No. 4,977,373 entitled "Barkhausen Noise Method for Determining Biaxial Stresses in Ferromagnetic Materials; U.S. Pat. No. 4,634,976 entitled "Barkhausen Noise method for Stress and Defect Detecting in Hard Steel"; and U.S. Pat. No. 4,599,563 entitled "Barkhausen Noise Method for Analyzing the Anisotropic Properties of Ferromagnetic Steel". One skilled in the art will appreciate however, that other rollscan inspection devices may be appropriately employed.

Rollscan inspection generally refers to a method of inspecting using magnetoelastic interactions, and originated while scanning for residual stress in rolls of material. The rollscan inspection device typically comprises a sensor designed to introduce an alternating magnetic field within a material and detect the Barkhausen noise created from the magnetoelastic interaction. The measured value is then converted into residual stress (KSI) measurement data. As used herein, the term magnetoelastic interactions generally refer to the interactions between stress and magnetic fields. Such magnetoelastic interactions create electrical pulses (i.e. Barkhausen Noise) that are produced by the movement of magnetic domains walls 139 in the magnetic field. In one embodiment of the present invention, an alternating magnetic field (not shown) may be applied so as to effect the magnetic domains 136 and move the domain walls 139 from an aligned state of equilibrium 138 to a continuous state of movement and generate the electrical pulses (not shown). The resulting electrical pulses are generally referred to as Barkhausen Noises.

As further illustrated in FIG. 1, the magnetic alignment 138 of magnetic domains 136 are influenced by the alternating magnetic field (not shown) generated by the sensor head 132, within a stressed material 110. Flux density forces are generally the energy-density of a ferromagnetic material, calculated while a magnetic field is applied to the material. The opposing movement of the magnetic field may facilitate movement of the domain walls, generating the Barkhausen Noises, or electrical pulses, and producing a measurement of the amount of stress in the material. In one aspect, where a magnetic field is applied to a material having compressive stresses (i.e. the material is being pushed together), the resulting Barkhausen Noises may be relatively low. In an alternate embodiment, where a magnetic field is applied to a material having relatively high tensile stresses (i.e. the material is being pulled apart), the resulting Barkhausen Noises may be relatively high. In another embodiment where a magnetic field is applied to a material having little or no stress, the resulting Barkhausen Noises may be measured at a relative level amid a compressive and tensile stress level.

Figure 2:
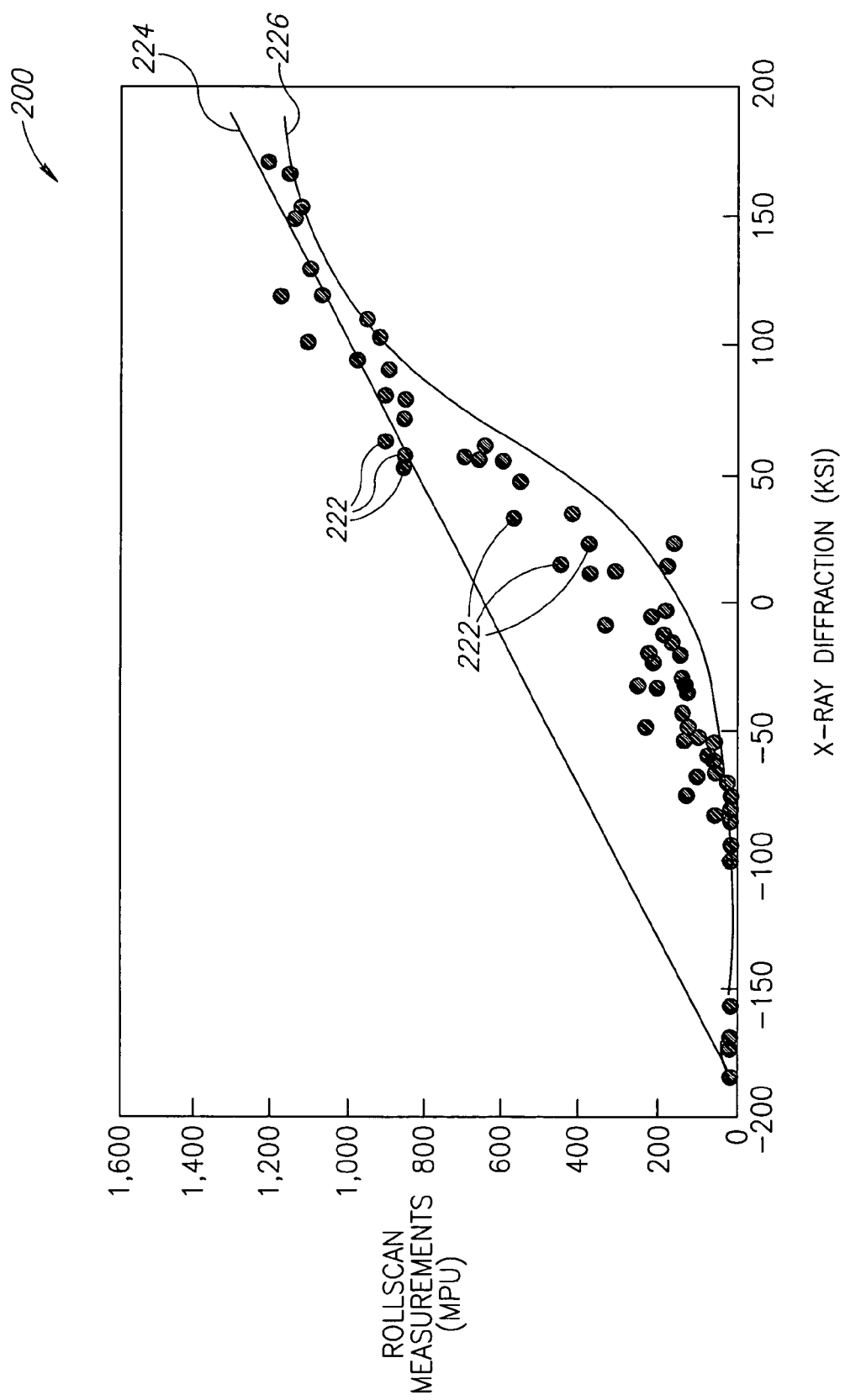
FIG. 2 is a graph showing x-ray diffraction versus rollscan measurements in a sample material, according to another embodiment of the invention.

FIG. 2 is a graph 200 showing x-ray diffraction versus rollscan measurements in accordance with an AERMET®100 alloy sample manufactured by Carpenter Technology Corporation. In this embodiment, the alloy sample is an iron-cobalt-nickel alloy that has been strengthened by carbon, chrome and molybdenum. The AERMET®100 alloy sample is equal in strength to 300M alloy but has increased fracture toughness and stress-corrosion cracking resistance. In one embodiment of the present invention, 300M alloy may be used for the metallic material to be measured for residual stress. 300M is a low alloy, vacuum-melted steel of very high strength. It is a modified steel material comprising silicon, vanadium, carbon and molybdenum. 300M has a very good combination of strength, toughness, fatigue strength and ductility. It is a through-hardening alloy that may be used for such components as aircraft landing gear, high strength bolts and airframe parts.

In one particular embodiment, rollscan inspection may be measured as magnetoelastic parameter units, MPUs, and may be plotted against diffraction peaks in KSI (kip per square inch) to create a plotted graph 200 that indicates a stress level. When used alone, the rollscan measurements provide an output in MPUs. In a theoretical sample of material, the magnitude of the Barkhausen Noise, or electrical pulses, has a direct correlation to the amount of residual stress. In general, the value of the electrical pulses for the theoretical sample 224 steadily increases from a stress of compression to tensile residual stress. In actual samples of material, however, a steady increase in electrical pulses is not as apparent, indicating that the magnitude of Barkhausen Noise is not an arbitrary linear description of the output of a rollscan inspection.

In order to tie the rollscan measurements to a known value of residual stress within a specimen under test, an empirical database is created. Actual rollscan and diffraction measurements 222 may be acquired using actual material specimens under test, this data may be plotted to determine the correlation of rollscan and diffraction data from specimens having known residual stress values to infer the value of residual stress within the actual material specimens under test. The empirical database may be created using diffraction measurements and rollscan measurements of a variety of material specimens having known residual stress values (tension and compression), and the resulting empirical correlation 226 may be plotted as shown on FIG. 2.

Figure 3:
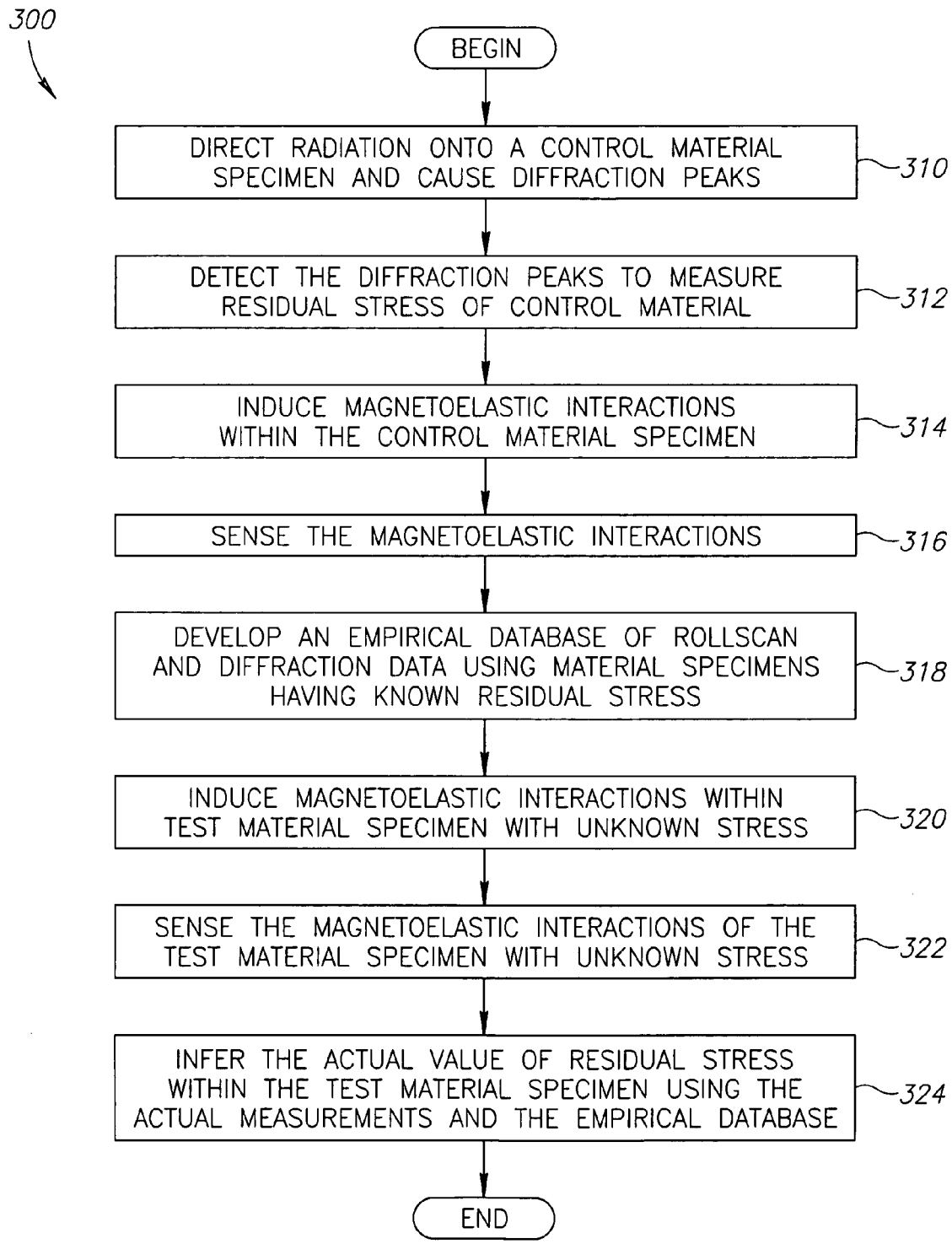
FIG. 3 is a block diagrammatic view of a method of measuring residual stress in a coated metallic material according to an alternate embodiment of the present invention.

FIG. 3 is a block diagrammatic view of method 300 of measuring residual stress in a material, according to an embodiment of the invention. At a block 310, radiation is directed onto a stressed material and diffraction peaks caused by the direct radiation are detected at a block 312 to measure known residual stress of a control specimen. As the term is used herein, control specimen may refer to a previously inspected, investigated stressed material, which is used as a developmental standard in measuring a material under test. In one particular embodiment, the stressed control material may include a material stressed by bending, including point bending, which clamps the material and induces stress through bending. At a block 314, magnetoelastic interactions are induced within the control material specimen, and the magnetoelastic interactions are sensed at block 316. At a block 318, the Barkhausen Noise, created by the magnetoelastic interactions, are combined with the diffraction peaks to develop an empirical database of rollscan and diffraction data, as previously described with reference to FIG. 1. A test material under inspection with an unknown stress level is induced with magnetoelastic interactions at a block 320. The magnetoelastic interaction output from the test material is sensed at a block 322. The actual residual level within the test material specimen is inferred using the magnetoelastic interaction output measurements and the empirical database at block 324.

Figure 4:
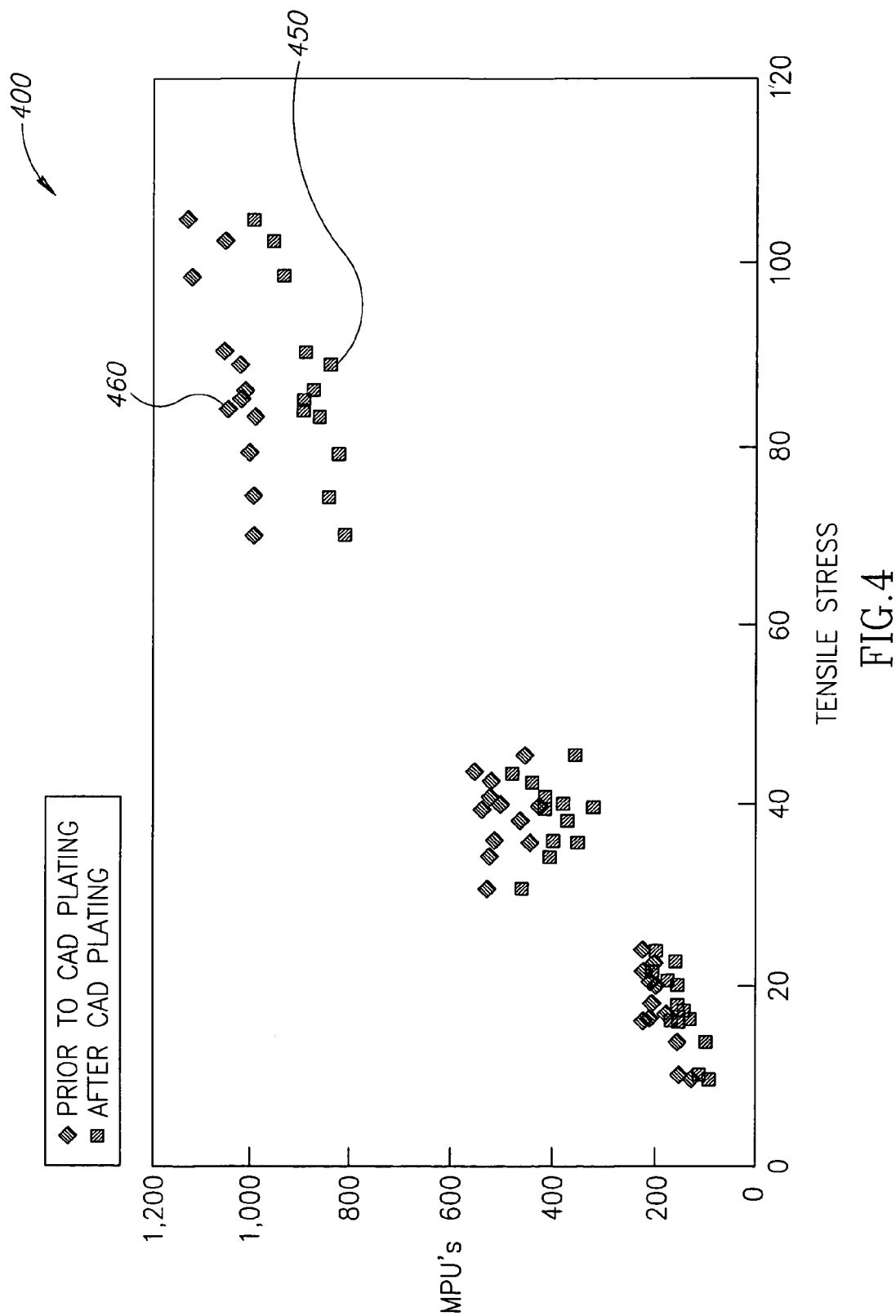
FIG. 4 is a graph showing diffraction versus rollscan measurements in a coated sample material, according to yet another embodiment of the invention.

FIG. 4 is a graph 400 showing actual residual stress versus rollscan measurements (MPUs) for both plated material specimens 450 and non-plated material specimens 460. It will be appreciated that material specimens may be plated (or coated) for various suitable reasons, including preventing the initiation of corrosion. Examples of suitable plating include cadmium plating, ion vapor deposit plating, and other suitable plating and coating layers. In one particular aspect, the present invention provides for measuring residual stress in a coated stressed material without the removal of the coating. The data shown in FIG. 4 suggest that embodiments of the present invention may provide improved residual stress measurements in comparison with the prior art Embodiments of the present invention may provide significant advantages over prior art residual stress and analysis. For example, embodiments of the present invention may provide for a meaningful and accurate analysis of the measurement of residual stress, and may overcome some of the disadvantages of previous methods. Embodiments of the present invention may also provide for a method of measuring residual stress in metallic materials with protective plating layers, including cadmium and ion vapor deposit plating, and protective coatings (including paint and primer) such that removal of the protective coat is no longer required, significantly reducing or eliminating the possibility of corrosion initiation in those parts stripped of the protective coat.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A method of determining residual stress in a stressed material, comprising:
    directing radiation onto the stressed material and causing diffraction peaks;
    detecting the diffraction peaks;
    inducing magnetoelastic interactions within the stressed material;
    sensing the magnetoelastic interactions; and
    combining the diffraction measurements and the magnetoelastic interaction output to generate a correlation between at least one of the diffraction peaks and the magnetoelastic interaction output within an empirical database developed using measurements from a plurality of specimens having known residual stress.

2. The method of claim 1, wherein detecting diffraction peaks includes detecting a plurality of angles of diffraction.

3. The method of claim 2, further including detecting at least one of tensile stress angles and compressive stress angles.

4. The method of claim 1, wherein inducing magnetoelastic interactions includes inducing an alternating magnetic field within the stressed material.

5. The method of claim 4, further including inducing external magnetic forces in opposing directions, including flux density forces.

6. The method of claim 1, wherein sensing the magnetoelastic interactions includes at least one of surface and subsurface inspection of the stressed material, further including scanning the stressed material.

7. The method of claim 1, wherein combining the diffraction peaks and the magnetoelastic interactions includes converting the peaks and interactions into graphical measurements to indicate a stress level.

8. The method of claim 1, further comprising applying at least one of a layer of coating or plating to the stressed material.

9. A method of measuring residual stress in a material under test, comprising:
    developing an empirical database using measurements from a plurality of specimens having known residual stress using at least one of diffraction values and magnetoelastic interaction values;
    inducing magnetoelastic interaction outputs within the material under test;
    sensing the magnetoelastic interaction outputs; and
    determining a residual stress within the material under test by correlating at least one of the diffraction peaks and the magnetoelastic interactions in the empirical database to the magnetoelastic interactions output.

10. The method of claim 9, wherein the material under test includes at least one of a layer of coating and plating.

11. The method of claim 9, wherein determining a residual stress includes combining the diffraction peaks and magnetoelastic interactions graphically to indicate a stress level.

12. A system for measuring residual stress in a stressed material, comprising:
    an electromagnetic assembly adapted to induce magnetoelastic interaction outputs within the stress material and to sense the induced magnetoelastic interaction outputs; and
    a data reduction system adapted to develop an empirical database of diffraction peaks from a radiation device and magnetoelastic interactions from an electromagnetic assembly and to determine a measured stress level based on a comparison with an empirical database and the magentoelastic interaction ouputs.

13. The system of claim 12, wherein the radiation device comprises an x-ray diffraction device.

14. The system of claim 12, wherein the diffraction peaks comprise a plurality of angles of diffraction, including at least one of tensile stress angles and compressive stress angles.

15. The system of claim 12, wherein the electromagnetic assembly includes a sensor head comprising a magnetizable member, a means for generating an alternating magnetic field within the magnetizable member, and a sensor adapted to sense at least a portion of the magnetoelastic interactions induced within the stressed material by the alternating magnetic field.

16. The system of claim 12, wherein the data reduction system includes an output system adapted to convert the diffraction peaks and magnetoelastic interactions into a graphical measurement to indicate a correlation between the empirical database and the magnetoelastic interaction output of the stressed material.

* * * * *